United States Patent
Patterson

(10) Patent No.: US 10,011,884 B2
(45) Date of Patent: Jul. 3, 2018

(54) METHODS AND SYSTEMS FOR PREDICTING WHETHER A SUBJECT HAS A CERVICAL INTRAEPITHELIAL NEOPLASIA (CIN) LESION FROM A SUSPENSION SAMPLE OF CERVICAL CELLS

(75) Inventor: Bruce K. Patterson, Palo Alto, CA (US)

(73) Assignee: IncellDx, Inc., Menlo Park, CA (US)

( * ) Notice: Subject to any disclaimer, the term of this patent is extended or adjusted under 35 U.S.C. 154(b) by 647 days.

(21) Appl. No.: 13/294,101

(22) Filed: Nov. 10, 2011

(65) Prior Publication Data

US 2012/0122078 A1 May 17, 2012

Related U.S. Application Data

(60) Provisional application No. 61/484,142, filed on May 9, 2011, provisional application No. 61/413,302, filed on Nov. 12, 2010.

(51) Int. Cl.
| | |
|---|---|
| *G01N 33/53* | (2006.01) |
| *G01N 33/52* | (2006.01) |
| *G01N 33/48* | (2006.01) |
| *C12Q 1/70* | (2006.01) |
| *G01N 33/574* | (2006.01) |
| *G01N 33/50* | (2006.01) |
| *G06F 19/20* | (2011.01) |
| *G06F 19/00* | (2018.01) |

(52) U.S. Cl.
CPC ......... *C12Q 1/708* (2013.01); *G01N 33/5091* (2013.01); *G01N 33/57411* (2013.01); *G06F 19/20* (2013.01); *G06F 19/345* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 7,524,631 B2 | 4/2009 | Patterson |
| 2003/0157482 A1 | 8/2003 | Keesee et al. |
| 2004/0260157 A1 | 12/2004 | Montes |
| 2005/0221399 A1 | 10/2005 | Nakano et al. |
| 2005/0260566 A1 | 11/2005 | Fischer et al. |
| 2006/0204071 A1 | 9/2006 | Ortyn et al. |
| 2008/0262384 A1 | 10/2008 | Wiederkehr et al. |
| 2009/0220945 A1 | 9/2009 | Patterson |
| 2010/0184046 A1 | 7/2010 | Klass et al. |
| 2012/0202200 A1 | 8/2012 | Changati et al. |

FOREIGN PATENT DOCUMENTS

| | | | |
|---|---|---|---|
| JP | 2005315862 A | 11/2005 | |
| JP | 2008528058 A | 7/2008 | |
| WO | WO 2006/048155 A1 | 5/2006 | |
| WO | WO 2006/052822 A2 | 5/2006 | |
| WO | WO2009057525 A1 | 5/2009 | |
| WO | WO2009151632 A1 | 12/2009 | |

OTHER PUBLICATIONS

Ling J et al. Application of flow cytometry for biomarker-based cervical cancer cells detection. Diagn Cytopathol. Feb. 2008;36(2):76-84. doi: 10.1002/dc.20763.*
David A. Basiji et al. Cellular Image Analysis and Imaging by Flow Cytometry. Clin Lab Med. Sep. 2007 ; 27(3): 653-viii.*
Cervical biopsy for abnormal cervical cell changes. Internet publication. Jan. 5, 2009.*
Evangelou et al. Electron microscopy evidence that cytoplasmic localization of the p16INK4A "nuclear" cyclindependent kinase inhibitor (CKI) in tumor cells is specific and not an artifact. A study in non-small cell lung carcinomas. Biotechnic & Histochemistry 2004, 79(1): 5-10.*
Veerman, Margot M. M.D. et al. "Clinical value of morphometric and DNA flow cytometric variables as independent predictors of survival in epithelial ovarian carcinoma: a 5-year follow-up study", International journal of gynecological pathology, 2009, vol. 28, No. 5, pp. 432-441. See the whole document, especially, abstract, pp. 432-434.
Grundhoefer et al., "Determination of Liquid-Based Cervical Cytology Specimen Adequacy Using Cellular Light Scatter and Flow Cytometry", Cytometry, vol. 46, No. 6, pp. 340-344 (2001).
Narimatsu et al., "High-Throughput Cervical Cancer Screening Using Intracellular Human Papillomavirus E6 and E7 mRMA Quantification by Flow Cytometry", American Journal of Clinical Pathology, vol. 123, No. 5, pp. 716-723 (2005).
Zuna et al., Comparison of Human Papillomavirus Genotypes in High-Grade Squamous Intraepithelial Lesions and Invasive Cervical Carcinoma: Evidence for Differences in Biologic Potential of Precursor Lesions, Mod Pathol 17 (11), 1314-1322.
Schmidt et al., Visual estimates of nucleus-to-nucleus ratios: can we trust our eyes to use the Bethesda ASCUS and LSIL size criteria?, Cancer. Oct. 25, 2008;114(5):287-93; abstract only.
Melsheimer et al., DNA aneuploidy and integration of human papillomavirus type 16 e6/e7 oncogenes in intraepithelial neoplasia and invasive squamous cell carcinoma of the cervix uteri, Clin Cancer Res. May 1, 2004;10(9):3059-63.

(Continued)

*Primary Examiner* — Nianxiang Zou
(74) *Attorney, Agent, or Firm* — Otto C. Guedelhoefer, IV; Bret E. Field; Bozicevic, Field & Francis LLP

(57) ABSTRACT

Methods of predicting whether a subject has a cervical intraepithelial neoplasia (CIN) lesion are provided. Aspects of the methods include obtaining both morphometric and biomarker data from a liquid cervical cellular sample and then using both types of data to predict whether the subject has a CIN lesion. Also provided are systems that find use in practicing the methods. The methods and systems find use in a variety of applications, including cervical cancer screening applications.

29 Claims, 8 Drawing Sheets

(56) References Cited

OTHER PUBLICATIONS

Drezek et al., Light scattering from cervical cells throughout neoplastic progression: influence of nuclear morphology, DNA content, and chromatin texture, J Biomed Opt. (2003) 8(1):7-16.
Krishan et al., Detection of tumor cells in body cavity fluids by flow cytometric and immunocytochemical analysis, Diagn Cytopathol. Aug. 2006;34(8):528-41.

* cited by examiner

E6, E7 + cells, High N/C ratio, pleiomorphic nuclei

E6, E7 - cells, low N/C ratio, round/regular nuclei

Combined E6, E7 mRNA and DNA Ploidy

Combined Morphometric and E6, E7 mRNA (x-axis)

Combined Morphometric and E6, E7 mRNA

SEQUENCE LISTING

<160> NUMBER OF SEQ ID NOS: 20

<210> SEQ ID NO 1
<211> LENGTH: 30
<212> TYPE: DNA

<213> ORGANISM: Artificial Sequence
<220> FEATURE:
<223> OTHER INFORMATION: Synthetic Probe

<400> SEQUENCE: 1
ttagggtaac atgtcttcca tgcatgttgt					30

<210> SEQ ID NO 2
<211> LENGTH: 31
<212> TYPE: DNA
<213> ORGANISM: Artificial Sequence
<220> FEATURE:
<223> OTHER INFORMATION: Synthetic Probe

<400> SEQUENCE: 2
acgttgctgt cacatccaca gcaacaggtc a				31

<210> SEQ ID NO 3
<211> LENGTH: 33
<212> TYPE: DNA
<213> ORGANISM: Artificial Sequence
<220> FEATURE:
<223> OTHER INFORMATION: Synthetic Probe

<400> SEQUENCE: 3
tgcaacaaga catacatcga ccggtccacc gac				33

<210> SEQ ID NO 4
<211> LENGTH: 30
<212> TYPE: DNA
<213> ORGANISM: Artificial Sequence
<220> FEATURE:
<223> OTHER INFORMATION: Synthetic Probe

<400> SEQUENCE: 4
ggttacaata ttgtaatggg ctctctccgg				30

<210> SEQ ID NO 5
<211> LENGTH: 30
<212> TYPE: DNA
<213> ORGANISM: Artificial Sequence
<220> FEATURE:
<223> OTHER INFORMATION: Synthetic Probe

<400> SEQUENCE: 5
tttcaggacc cacaggagcg acccagaaag				30

<210> SEQ ID NO 6
<211> LENGTH: 36
<212> TYPE: DNA
<213> ORGANISM: Artificial Sequence
<220> FEATURE:
<223> OTHER INFORMATION: Synthetic Probe

<400> SEQUENCE: 6
tcgagcacga atggcactgg cctctatagt gcccag				36

<210> SEQ ID NO 7
<211> LENGTH: 34
<212> TYPE: DNA
<213> ORGANISM: Artificial Sequence
<220> FEATURE:
<223> OTHER INFORMATION: Synthetic Probe

<400> SEQUENCE: 7
ggtcaaccgg aatttcattt tggggctcta aatg				34

<210> SEQ ID NO 8
<211> LENGTH: 30
<212> TYPE: DNA
<213> ORGANISM: Artificial Sequence
<220> FEATURE:
<223> OTHER INFORMATION: Synthetic Probe

<400> SEQUENCE: 8
cttggcacaa atcatgcaat gttcgtggtt                                    30

<210> SEQ ID NO 9
<211> LENGTH: 30
<212> TYPE: DNA
<213> ORGANISM: Artificial Sequence
<220> FEATURE:
<223> OTHER INFORMATION: Synthetic Probe

<400> SEQUENCE: 9
gtcctgaaac attgcagttc tcttttggtg                                    30

<210> SEQ ID NO 10
<211> LENGTH: 30
<212> TYPE: DNA
<213> ORGANISM: Artificial Sequence
<220> FEATURE:
<223> OTHER INFORMATION: Synthetic Probe

<400> SEQUENCE: 10
ctgtgcataa ctgtggtaac tttctgggtc                                    30

<210> SEQ ID NO 11
<211> LENGTH: 30
<212> TYPE: DNA
<213> ORGANISM: Artificial Sequence
<220> FEATURE:
<223> OTHER INFORMATION: Synthetic Probe

<400> SEQUENCE: 11
tcacacaacg gtttgttgta ttgctgttct                                    30

<210> SEQ ID NO 12
<211> LENGTH: 30
<212> TYPE: DNA
<213> ORGANISM: Artificial Sequence
<220> FEATURE:
<223> OTHER INFORMATION: Synthetic Probe

<400> SEQUENCE: 12
tgggtttctc tacgtgttct tgatgatctg                                    30

<210> SEQ ID NO 13
<211> LENGTH: 30
<212> TYPE: DNA
<213> ORGANISM: Artificial Sequence
<220> FEATURE:
<223> OTHER INFORMATION: Synthetic Probe

<400> SEQUENCE: 13
taacaggtct tccaaagtac gaatgtctac                                    30

<210> SEQ ID NO 14
<211> LENGTH: 30
<212> TYPE: DNA
<213> ORGANISM: Artificial Sequence
<220> FEATURE:

```
<223> OTHER INFORMATION: Synthetic Probe

<400> SEQUENCE: 14
tatggtttct gagaacagat ggggcacaca                                    30

<210> SEQ ID NO 15
<211> LENGTH: 30
<212> TYPE: DNA
<213> ORGANISM: Artificial Sequence
<220> FEATURE:
<223> OTHER INFORMATION: Synthetic Probe

<400> SEQUENCE: 15
agtgttcagt tccgtgcaca gatcaggtag                                    30

<210> SEQ ID NO 16
<211> LENGTH: 30
<212> TYPE: DNA
<213> ORGANISM: Artificial Sequence
<220> FEATURE:
<223> OTHER INFORMATION: Synthetic Probe

<400> SEQUENCE: 16
cctctgtaag ttccaatact gtcttgcaat                                    30

<210> SEQ ID NO 17
<211> LENGTH: 30
<212> TYPE: DNA
<213> ORGANISM: Artificial Sequence
<220> FEATURE:
<223> OTHER INFORMATION: Synthetic Probe

<400> SEQUENCE: 17
cctctatagt gcccagctat gttgtgaaat                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic Probe

<400> SEQUENCE: 18
ttgtgtttct ctgcgtcgtt ggagtcgttc                                    30

<210> SEQ ID NO 19
<211> LENGTH: 28
<212> TYPE: DNA
<213> ORGANISM: Artificial Sequence
<220> FEATURE:
<223> OTHER INFORMATION: Synthetic Probe

<400> SEQUENCE: 19
ctggcttcac acacaacaca tacacaac                                      28

<210> SEQ ID NO 20
<211> LENGTH: 30
<212> TYPE: DNA
<213> ORGANISM: Artificial Sequence
<220> FEATURE:
<223> OTHER INFORMATION: Synthetic Probe

<400> SEQUENCE: 20
tgctcgaagg tcgtctgctg agctttctac                                    30
```

METHODS AND SYSTEMS FOR PREDICTING WHETHER A SUBJECT HAS A CERVICAL INTRAEPITHELIAL NEOPLASIA (CIN) LESION FROM A SUSPENSION SAMPLE OF CERVICAL CELLS

CROSS-REFERENCE TO RELATED APPLICATIONS

Pursuant to 35 U.S.C. § 119 (e) this application claims priority to the filing date of U.S. Provisional Patent Application Ser. No. 61/484,142 filed May 9, 2011 and U.S. Provisional Patent Application Ser. No. 61/413,302 filed on Nov. 12, 2010; the disclosures of which applications are herein incorporated by reference.

INTRODUCTION

The Papanicolaou (PAP) smear has been the cornerstone of cervical cancer screening since 1949. By definition, the PAP smear is a stain performed on cells smeared on a slide and visualized by microscopy. Following the advent of liquid-based cervical cytology (LBC), cells from the cervix were obtained using a brush, suspended in a fixative solution, and then applied to a slide prior to staining. Highly trained cytotechnologists and cytopathologists review the stained slides looking for evidence of abnormal cells as indicated by the characteristics in Table 1.

TABLE 1

| Low grade squamous intraepithelial lesion (LSIL) | High grade squamous intraepithelial lesion (HSIL) |
|---|---|
| Caviation | (Moderate-Marked increase) N/C* Ratio |
| (Mild increase) N/C Ratio Hyperchromasia | Coarse Chromatin Hyperchromasia Irregular Nuclear Contour Single Abn Cells Syncytial Aggregates Pleomorphism |

*N/C = nuclear to cytoplasmic ratio.

Because of the necessity to use slides for the PAP smear, other biomarkers used for cervical cancer screening, especially those used for the molecular detection of HPV DNA, are performed on a separate aliquot of the LBC. Though some biomarkers such as p16 can be performed on a slide, the throughput is not desirable to accommodate the 60-70 million cervical cytology specimens obtained every year in the US and the 150+ million samples worldwide. Further, molecular techniques performed on a slide are cumbersome and time consuming, characteristics that are not amenable to cervical cancer screening.

Clinically, the PAP smear and HPV testing are used together though they are very disparate technologies. The PAP smear has relatively low sensitivity (50%) and relatively high specificity (90%) for high grade cervical lesions (pre-cervical cancer and cervical cancer). Conversely, HPV DNA testing has high sensitivity (>90%) but low specificity (30%) for high grade cervical lesions (pre-cervical cancer and cervical cancer. These performance characteristics have supported the combined use of these tests for effective cervical cancer screening. Some investigators have pushed for the sole use of HPV detection for cervical cancer screening (primary HPV screening), however, current HPV DNA tests lack the specificity afforded by morphologic assessment using PAP smear, raising a concern for an overwhelming number of unnecessary colposcopy/biopsy procedures. Thus the replacement of the PAP smear by HPV testing alone remains extremely controversial.

SUMMARY

Methods of predicting whether a subject has a cervical intraepithelial neoplasia (CIN) lesion are provided. Aspects of the methods include obtaining morphometric data as well as biomarker data and/or non-specific cell data from a liquid cervical cellular sample by assaying the sample in suspension, and then using the different types of data to predict whether the subject has a CIN lesion. Also provided are systems that find use in practicing the methods. The methods and systems find use in a variety of applications, including cervical cancer screening applications.

BRIEF DESCRIPTION OF THE FIGURES

FIG. 3A shows that cells having a high N/C ratio are E6/E7 positive and have abnormal DNA content. FIG. 3B shows that cells having a low N/C ratio are E6/E7 negative and have a normal DNA content.

FIG. 5A shows dot plots of N/C ratios versus DNA content of normal cervical cells (top panel) and LSIL cervical cells (bottom panel).

DETAILED DESCRIPTION

Figure 1:
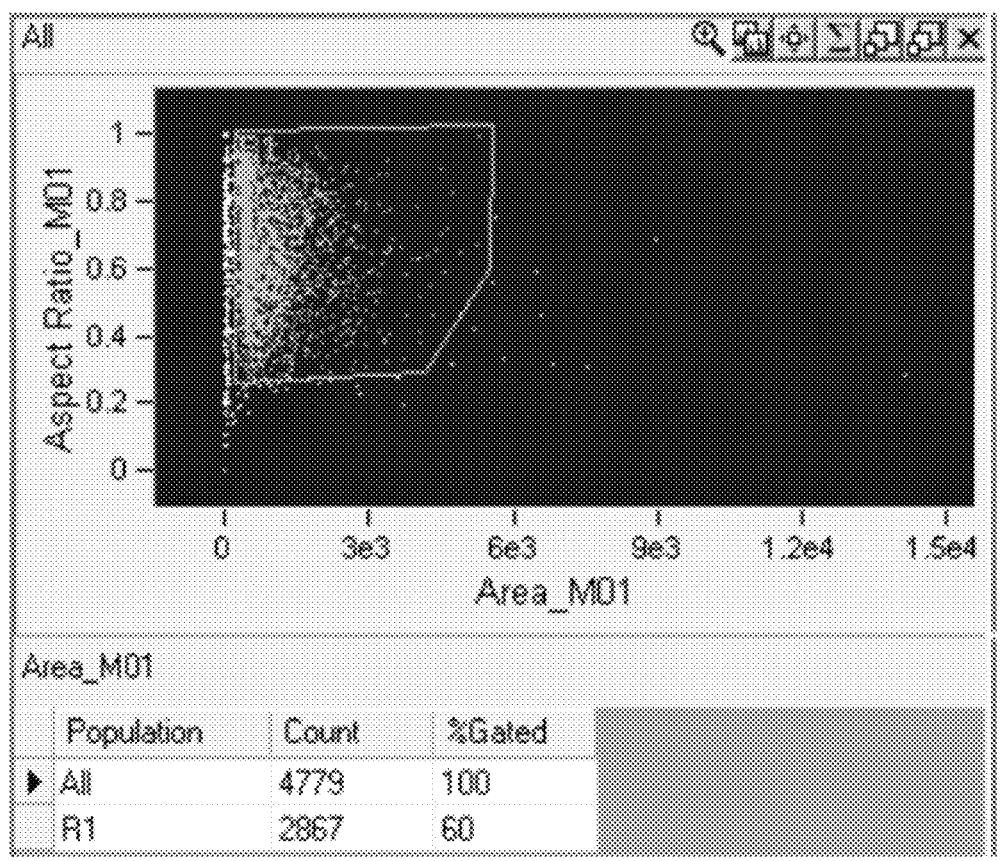
FIG. 1 shows instrument set-up for using Aspect Ratio versus Area dot plot to identify intact single cells (gated) in a liquid-based cervical cytology (LBC) specimen.

Methods of predicting whether a subject has a cervical intraepithelial neoplasia (CIN) lesion are provided. Aspects of the methods include obtaining morphometric as well as biomarker data and/or non-specific cell data from a liquid cervical cellular sample by assaying the sample in suspension, and then using the different types of data to predict whether the subject has a CIN lesion. Also provided are systems that find use in practicing the methods. The methods and systems find use in a variety of applications, including cervical cancer screening applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the invention, aspects of embodiments of the methods will be described first in greater detail. Next, embodiments of systems that may be used in practicing methods of the invention are reviewed.

Methods

As summarized above, embodiments of the invention are directed to methods of predicting whether a subject has a cervical intraepithelial neoplasia (CIN) lesion or cervical cancer. The term "CIN lesion" (also referred to in the art as cervical dysplasia) is used in its conventional sense to refer to the abnormal growth of squamous cells on the surface of the cervix. As is known in the art, CIN lesions may be histologically graded as CIN1, CIN2/3, CIN2 and CIN3. CIN1 lesions are those lesions that are confined to the basal ⅓ of the epithelium, and have the least risk of developing into a cancerous lesion, relative to the other categories of lesions. CIN2 lesions are characterized by moderate dysplasia confined to the basal ⅔ of the epithelium. CIN3 lesions (sometimes referred to by those of skill in the art as cervical carcinoma in situ) are categorized by the presence of severe dysplasia that traverses more than ⅔ of the epithelium. The CIN2/3 category (i.e., CIN2+) collectively refers to both CIN2 and CIN3 lesions.

Embodiments of the invention are characterized by predicting the presence of a CIN lesion in a subject with a high degree of sensitivity and specificity. By predicting is meant to prognosticate or foresee the presence of a CIN lesion in the subject without actually taking a biopsy of the cervix of the subject. The terms sensitivity and specificity are used in their conventional sense. As such, sensitivity is a measure of the proportion of actual positives (as opposed to false positives) that are correctly identified while specificity is a measure of negatives which are correctly identified. Embodiments of the invention may predict the presence or absence of any type of CIN lesion. Embodiments of the invention may also predict the type of CIN lesion, e.g., whether the CIN lesion is a CIN1, CIN2+, CIN2 or CIN3 lesion. Embodiments of the methods make this prediction, e.g., whether a lesion is present, what type of lesion is present (such as whether a CIN2+ lesion is present) with a high degree of sensitivity and specificity. In some instances, sensitivity is 85% or more, such as 90% or more, including 95% or more. In some instances, specificity is 85% or more, such as 87% or more, including 90% or more.

Aspects of the methods include obtaining both: (1) morphometric data and (2) biomarker data and/or non-specific cell data from a labeled liquid sample of cervical cells in suspension from the subject, e.g., a liquid sample labeled with one or both of a biomarker label and a non-specific cell label. In other words, a liquid sample of cervical cells is collected from the subject, where the cervical cells are in suspension in a fluid medium (e.g., as described in greater detail below), is assayed to obtain both morphometric data and biomarker/non-specific cell data. Thus, a labeled liquid sample according to aspects of the methods may be a biomarker labeled liquid sample, a non-specific cell labeled liquid sample, or a biomarker and non-specific cell labeled liquid sample. The labeled liquid sample of cervical cells that is assayed may be provided according to any convenient protocol.

In one embodiment, an initial fluid cervical cellular sample is prepared by taking a cellular sample from the cervix and combining it with a suitable fluid medium. Any convenient protocol for collecting cervical cells may be employed. Examples of protocols of interest include protocols that employ a cervical brush or broom device to collect cells from the surface of the cervix and the endocervix. Descriptions of examples of cervical cell collection devices that may find use in methods of the invention are provided in U.S. Pat. Nos. 2,955,591; 3,626,470; 3,815,580; 3,877,464; 3,881,464; 3,945,372; 4,127,113; 4,175,008; 4,700,713; 4,754,764; 4,762,133; 4,754,764; 4,873,992; 4,862,899; 4,953,560; 5,445,164; 5,787,891; 5,795,309; 6,387,058 and 6,740,049.

Following collection, the cellular sample may be combined with a suitable liquid medium, as desired. Liquid mediums of interest include, but are not limited to: saline, or balanced salt, solutions (such as Hanks' balanced salt solution, a minimal essential (MEM) tissue culture medium, POLYSAL™ solution, and normal saline); cytology mediums, e.g., Universal Collection Medium (UCM); the universal collection medium described in U.S. Pat. No. 7,371,518 (the disclosure of which is herein incorporated by reference); Standard Transport Medium (STM), PRESERVCYT™ fluid medium (Cytyc, Inc. (Boxborough, Mass.)); CytoRich™ fluid medium (TriPath, Inc. (Burlington, N.C.); and the like.

Where desired, the collected initial sample may be assessed for adequacy prior to proceeding further in the process. For example, an aliquot of the sample may be subjected to light scatter analysis to determine whether adequate target cells are present in the sample, e.g., as described in U.S. Pat. No. 6,329,167; the disclosure of which is herein incorporated by reference.

Following preparation, the resultant initial fluid cervical cellular sample may be fixed and/or permeabilized as desired. As such, methods of the invention include fixing the cellular sample by contacting the sample with a suitable fixation reagent. Fixation reagents of interest are those that fix the cells at a desired timepoint. Any convenient fixation reagent may be employed, where suitable fixation reagents include, but are not limited to: formaldehyde, paraformaldehyde, formaldehyde/acetone, methanol/acetone, IncellFP (IncellDx, Inc) etc. For example, paraformaldehyde used at a final concentration of about 1 to 2% has been found to be a good cross-linking fixative. In some instances, the cells in the sample are permeabilized by contacting the cells with a permeabilizing reagent. Permeabilizing reagents of interest are reagents that allow the labeled biomarker probes, e.g., as described in greater detail below, to access to the intracellular environment. Any convenient permeabilizing reagent may be employed, where suitable reagents include, but are not limited to: mild detergents, such as Triton X-100, NP-40, saponin, etc.; methanol, and the like. It may also be desirable to label cells with a positive heavy metal control, e.g. a DNA intercalator labeled with a heavy metal, e.g. iridium, etc. Cells may also be stained with a viability dye prior to fixation, e.g. ethidium bromide, propidium iodide, DAPI, $RhCl_3$, etc., as desired.

In certain embodiments, and as reviewed above, the sample that is assayed to obtain morphometric and biomarker data is a biomarker labeled sampled. Accordingly, the sample is one that has been labeled for one or more biomarkers of interest. By "biomarker labeled sample" is meant a sample which has been contacted with a labeled biomarker probe (e.g., as described in greater detail below) that specifically binds to a biomarker of interest if the biomarker is present in the cellular sample. Biomarkers of interest include, but are not limited to, cervical cancer biomarkers. Cervical cancer biomarkers are a distinctive biological or biologically derived indicator, for example nucleic acids or proteins, whose presence is associated or linked with either the propensity of a subject to develop cervical cancer or the presence of cervical cancer in a subject. Accordingly, biomarkers of interest include nucleic acid and protein analytes whose presence and/or amount in a cell can be used to make a prediction of at least the propensity of a subject to suffer from cervical cancer. Biomarkers of interest include, but are not limited to: HPV expression products of HPV genes, such as HPV genes L1, L2, E2, E4, E5, E6 or E7; cyclin-dependent kinase inhibitors, e.g., p14, $p15^{INK4b}$, p16 (i.e., $p16^{INK4a}$ as described in Serrano, M., et al., Nature, 1993 Dec. 16; 366(6456): 704-7), $p18^{INK4c}$, $p19^{INK4d}$, $p21^{WAF1/CIP1}$ and $p27^{KIP1}$; cell cycle regulatory proteins, e.g., $p14^{ARF}$; specific microRNAs or chromosome alterations 3q-associated with cervical cancer, such as described in United States Patent Publication No. 20100234445 (the disclosure of which is herein incorporated by reference); etc.

The biomarker labeled liquid cervical cellular sample that is assayed in methods of the invention may be prepared using any convenient labeling protocol. In some embodiments, preparation of the biomarker labeled liquid sample includes contacting an initial cervical cell sample with a labeled biomarker probe that specifically binds to a cervical cancer biomarker. Depending on the particular assay to be performed, the initial sample may be combined with a single labeled biomarker probe or two or more distinct labeled biomarker probes that bind to different biomarkers of different molecular composition, where the number of such distinct labeled biomarker probes may be two or more, e.g., three or more, four or more, five or more, etc; e.g., where the assay is a multiplex assay for two or more biomarkers.

In contacting the initial sample with the labeled biomarker probe(s), the sample is combined with one or more labeled biomarker probes to produce a reaction mixture. Labeled biomarker probes of interest include a specific binding domain and a label domain. The specific binding domain comprises a capture ligand that specifically binds to the biomarker of interest. Depending on the particular assay, the biomarker of interest may be a variety of different types of molecules, including but not limited to: proteins, polypeptides, proteoglycans, glycoproteins and the respective fragments of these molecules; nucleic acids, e.g., DNA and RNA, such as mRNA, etc. The capture ligand is therefore a ligand that binds to the biomarker molecule of interest, wherein this capture ligand may of course vary depending on the specific type of biomarker molecule to be detected, e.g., antibody for protein biomarker, oligonucleotide for mRNA biomarker. In certain embodiments, the affinity between a capture ligand and the biomarker molecule to which it specifically binds when they are specifically bound to each other in a binding complex is characterized by a $K_D$ (dissociation constant) of $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less.

As indicated above, a variety of different types of specific binding agents may be employed as the capture ligands, where the particular type of binding agent is selected based, at least in part, on the particular type of molecule of the biomarker of interest. Specific binding agents of interest include antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. Nucleic acid binding agents of interest are nucleic acids that specifically bind to biomarker nucleic acids in a cell. The length of these nucleic acids may vary, so long as it is sufficient for the oligonucleotide to serve as a specific binding agent, and in some instances ranges from 13 to 100 nt, such as 14 to 50 nt, e.g., 15 to 25 nt. The oligonucleotides that make up these nucleic acid binding agents may be DNA or RNA, or a synthetic analogue thereof, as desired.

In addition to the specific binding domain, the labeled biomarker probes further include a detectable label. Of interest as detectable labels are fluorescent dyes. Fluorescent dyes (fluorophores) can be selected from any of the many dyes suitable for use in imaging applications (e.g., flow cytometry). A large number of dyes are commercially available from a variety of sources, such as, for example, Molecular Probes (Eugene, Oreg.) and Exciton (Dayton, Ohio). Examples of fluorophores of interest include, but are not limited to, 4-acetamido-4'-isothiocyanatostilbene-2,2' disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcoulurarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

Where multiple distinct labeled biomarker probes are employed, the label of each distinct probe may be chosen to provide a distinguishable signal. For example, in embodiments where first and second distinct labeled biomarker probes are employed, the label in the second probe is a fluorescent label which produces a fluorescent signal that is distinguishable from the first fluorescent signal of the label of the first probe. Accordingly, the first and second fluorescent signals produced upon excitation of the first and second fluorescent labels are distinguishable from each other, meaning that both can be detected at the same time and that the signal from one does not modify or change the signal from the other. Each distinct label may produce signals that are distinguishable from any other label. For example, the cells may be stained with a third fluorescent label which produces a third fluorescent signal that is distinguishable from the first and second fluorescent signals.

In some instances, the labeled biomarker probe that is employed is an HPV E6, E7 oligonucleotide fluorescently labeled probe. Such probes may vary in length, ranging in some instances from 13 to 100 nt, such as 14 to 50 nt, e.g., 15 to 25 nt. The particular sequence of such probes may vary. Specific sequences of interest include, but are not limited to those found in the probe cocktail of the HPV OncoTect™ E6, E7 mRNA Detection Kit (incellDx, Menlo Park, Calif.).

Exemplary probe sequences specific for HPV E6/E7 gene (or mRNA) include those described in Faulkner-Jones et al. (J. Virol Methods 1993 vol. 41 pages 277-296; incorporated herein by reference). The sequences from Table 1 of Faulkner-Jones et al., which shows such exemplary HPV E6/E7 specific probe sequences, are provided below.

| HPV Type | Region | Sequence (5'-3') |
|---|---|---|
| 6b/11 | E6 + E7 | TTAGGGTAACATGTCTTCCATGCATGTTGT (SEQ ID NO: 01) |
|  | E7 | ACGTTGCTGTCACATCCACAGCAACAGGTCA (SEQ ID NO: 02) |
| 16 | E6 | TGCAACAAGACATACATCGACCGGTCCACCGAC (SEQ ID NO: 03) |
|  | E7 | GGTTACAATATTGTAATGGGCTCTCTCCGG (SEQ ID NO: 04) |
|  | E6 | TTTCAGGACCCACAGGAGCGACCCAGAAAG (SEQ ID NO: 05) |
| 18 | E6 + E7 | TCGAGCACGAATGGCACTGGCCTCTATAGTGCCCAG (SEQ ID NO: 06) |
|  | E7 | GGTCAACCGGAATTTCATTTTGGGGCTCTAAATG (SEQ ID NO: 07) |
| 33 | E6 | CTTGGCACAAATCATGCAATGTTCGTGGTT (SEQ ID NO: 08) |

Additional exemplary probe sequences for HPV E6/E7 include those described in Plummer et al. (Diagnostic Mol. Path. 1998 vol. 7, pages 76-84; incorporated herein by reference). The sequences from Table 1 in Plummer et al., which shows such exemplary HPV E6/E7 probe sequences, are provided below.

| HPV Type | Region | Sequence (5'-3') |
|---|---|---|
| HPV16 | E6 | GTCCTGAAACATTGCAGTTCTCTTTTGGTG (SEQ ID NO: 09) |
|  | E6 | CTGTGCATAACTGTGGTAACTTTCTGGGTC (SEQ ID NO: 10) |
|  | E6 | TCACACAACGGTTTGTTGTATTGCTGTTCT (SEQ ID NO: 11) |
|  | E6/E7 | TGGGTTTCTCTACGTGTTCTTGATGATCTG (SEQ ID NO: 12) |
|  | E7 | TAACAGGTCTTCCAAAGTACGAATGTCTAC (SEQ ID NO: 13) |
|  | E7 | TATGGTTTCTGAGAACAGATGGGGCACACA (SEQ ID NO: 14) |
| HPV18 | E6 | AGTGTTCAGTTCCGTGCACAGATCAGGTAG (SEQ ID NO: 15) |
|  | E6 | CCTCTGTAAGTTCCAATACTGTCTTGCAAT (SEQ ID NO: 16) |
|  | E6 | CCTCTATAGTGCCCAGCTATGTTGTGAAAT (SEQ ID NO: 17) |
|  | E6/E7 | TTGTGTTTCTCTGCGTCGTTGGAGTCGTTC (SEQ ID NO: 18) |
|  | E7 | CTGGCTTCACACI7ACAACACATACACAAC (SEQ ID NO: 19) |
|  | E7 | TGCTCGAAGGTCGTCTGCTGAGCTTTCTAC (SEQ ID NO: 20) |

Additional HPV specific probe sequences that find use in the methods and systems described herein may be designed and tested using any convenient probe design methodology.

In preparing the reaction mixture, the sample may be combined with the labeled biomarker probes using any convenient protocol. Combination may be carried out with mixing, as desired. Contact of the sample with the labeled biomarker probes is performed under incubation conditions that provide for binding of probes to their respective biomarkers, if present, in the sample. In some instances, the probes and samples are contacted and combined at a temperature ranging from 15 to 50, such as from 20 to about 40° C. Contact may be performed with mixing or agitation, e.g., with vortexing etc., to provide for sufficient combination of the reaction components and the sample.

The resultant reaction mixture may then be maintained or incubated for a period of time prior to assay for morphometric and biomarker data, e.g., via flow cytometric analysis (e.g., as described in greater detail below). In some instances, the reaction mixture is incubated at a temperature ranging from 15 to 50, such as from 20 to about 40° C. for a period of time ranging from about 30 minutes to 72 hours, such as 1 hour to 24 hours, including 1 hour to 3 hours. Following the above incubation step, the sample may be assayed immediately or stored for assay at a later time. If stored, in some embodiments the sample is stored at a reduced temperature; e.g., on ice.

Where desired, the resultant reaction mixture may be washed, e.g., to remove any unbound probes and other sample components. Washing may be performed using any convenient protocol, e.g., by combining the reaction mixture with a suitable wash buffer and separating the cells from the fluid. A given washing protocol may include one or more distinct washing steps, as desired. Following any washing protocol, the labeled cells may be re-suspended in a suitable liquid, e.g., the washing buffer or another buffer, for subsequent analysis, e.g., via flow cytometric analysis.

In some embodiments, as described above, the labeled liquid cell sample is labeled (or stained) with a non-specific cell stain, either in addition to or in the absence of a biomarker label. The cells may be stained with a non-specific stain using any convenient protocol. Of interest as non-specific cells stains are DNA specific stains. Dyes and stains that are specific for DNA (or preferentially bind double stranded polynucleotides in contrast to single-stranded polynucleotides) and therefore may be employed as non-specific stains include, but are not limited to: Hoechst 33342 (2'-[4-ethoxyphenyl]-5-[4-methyl-1-piperazinyl]-2, 5'-bi-1H-benzimidazole) and Hoechst 33258 (2'-[4-ethoxyphenyl]-5-[4-methyl-1-piperazinyl]-2,5'-bi-1H-benzimidazole) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyactridine. Depending on the particular stain and assay, the stain may serve in quantitation of biomarker, as an indication of cell cycle, etc.

Following preparation of the labeled sample, e.g., as described above, the sample is assayed to obtain both morphometric as well as biomarker and/or non-specific cell data. In some instances, the same aliquot of sample, i.e., the same physical quantity of sample, is assayed to obtain both the morphometric and biomarker/non-specific cell data. Accordingly, these embodiments are distinguished from protocols in which a first aliquot of a sample is assayed using one protocol, e.g., slide based protocol, for morphometric data and a second aliquot of the sample is assayed using another protocol, e.g., flow cytometric protocol.

Morphometric data refers to any type of data from which cell morphology information, i.e., information about the size, shape and/or structure of the cells, may be derived. Morphometric data of interest includes, but is not limited to data selected from the group consisting of: forward light scatter data, side light scatter data, image data and combinations thereof. Morphological parameters of interest include, but are not limited to: nuclear area, perimeter, texture or spatial frequency content, centroid position, shape (i.e., round, elliptical, barbell-shaped, etc.), volume, and ratios of any of these parameters. The obtained morphometric date may be for cells as a whole or for subparts thereof, e.g., the cytoplasm of cells. In some instances, the morphometric data may include an actual designation of whether a cell is normal or abnormal, including the type of abnormal cell. For example, morphometric data may, in some instances, include a designation that a given cell is abnormal, for example that the cell is: an atypical squamous cell, e.g., atypical squamous cell of undetermined significance (ASC-US), atypical squamous cell—cannot exclude HSIL (ASC-H); low grade squamous intraepithelial lesion (LGSIL or LSIL); high grade squamous intraepithelial lesion (HG-SIL or HSIL); squamous cell carcinoma; atypical glandular cell not otherwise specified (AGC-NOS); atypical clandular cell, suspicious for AIS or cancer (AGC-neoplastic); and adenocarcinoma in situ (AIS).

Biomarker data refers to any type of data from which biomarker information for the cell may be derived. In some instances, biomarker data is data that includes a signal emitted by the label of the labeled biomarker probe that is employed in the assay. The biomarker data may be in the form of the presence and amplitude of emitted light, the number of discrete positions in a cell or other object from which the light signal(s) originate(s), the relative placement of the signal sources, and the color (wavelength or waveband) of the light emitted at each position in the cell. The biomarker data may take the form of qualitative, semi-quantitative or quantitative data. Qualitative data is simply the presence or absence of the biomarker. Semi-quantitative or quantitative data is data that provides some indication of the amount, e.g., copy number, concentration, etc., of the biomarker in the cell. For example, semi-quantitative data may take the form of an indication that the copy number of a biomarker of interest is above a certain threshold number. Quantitative data provides an indication of an absolute value, e.g., copy number, amount, etc., of the biomarker in the cell. Semi-quantitative and quantitative data may be collectively referred to as biomarker quantitation data.

In some instances, the biomarker of interest is an mRNA that is present when a subject is infected with a high risk HPV strain. mRNAs of interest include an HPV E6, E7 mRNA. In these embodiments, the absolute copy number of the mRNA species of interest may be determined, such that the quantitation data of the mRNA species of interest is obtained. In some instances where the biomarker is HPV E6, E7, the total amount of E6, E7 mRNA species per cell is determined. In these instances, of interest is the identification of cells that 2 or more, such as 5 or more, including 10 or more, 50 or more, 100 or more, 200 or more, 500 or more HPV E6, E7 mRNA copies per cell, as these cells may be associated with the presence of a CIN lesion in the host. In some instances, the biomarker data that is obtained in methods of the invention provides information that there are 2 to 1000 copies of HPV E6, E7 mRNA per cell, e.g., 5 to 750 copies of HPV E6, E7 mRNA per cell, including 10 to 500 copies of HPV E6, E7 mRNA per cell. In some instances, the biomarker data that is obtained is the HPV E6, E7 mRNA copy number per cell data as described in U.S. Pat. No. 7,524,631, the disclosure of which is herein incorporated by reference. Determination of the copy number may include comparing a single to a suitable control, e.g. as provided by a non-specific DNA stain (such as described below), by a reference value, etc.

In some instances, photometric measurements are also obtained. Photometric measurements enable the determination of nuclear optical density, cytoplasm optical density, background optical density, and the ratios of any of these values.

Non-specific cell data is any type of data from which non-specific (i.e., non-biomarker specific) cell information for the cells in the sample may be derived. In some instances, non-specific cell data is data that includes a signal emitted by a non-specific cell stain that is employed in the assay. The non-specific cell data may be in the form of the presence and amplitude of emitted light, the number of discrete positions in a cell or other object from which the light signal(s) originate(s), the relative placement of the signal sources, and the color (wavelength or waveband) of the light emitted at each position in the cell. The non-specific cell data may take the form of qualitative, semi-quantitative or quantitative data. For example, quantitative or semi-quantitative non-specific cell data may include data on the DNA content of a cell obtained using a DNA stain (e.g., as described above). Other quantitative data includes electronic volume (EV). Thus, non-specific cell data may provide an indication of an absolute or relative value, e.g., copy number, amount, etc., of the non-specific cell component in the cell. Semi-quantitative and quantitative data may be collectively referred to as non-specific cell quantitation data. Qualitative non-specific cell data can provide information with respect to the presence of absence of a particular feature of a cell. For example, in cells stained with a DNA stain, the presence or absence of a cell nucleus can be determined (e.g., the number of nucleated cells in a sample, also referred to as percent nucleation).

It is noted that where multiple distinct labels are to be detected in a single labeled liquid cell sample, e.g., biomarker probe labels and non-specific cell stains used in a single sample, the labels and stains employed may be chosen to provide a distinguishable signal (as described above for using multiple biomarker probes in a single sample, above). For example, in embodiments where a labeled biomarker probe and a DNA stain are employed, the label for the biomarker probe is a fluorescent label which produces a fluorescent signal that is distinguishable from the fluorescent signal of the DNA stain. Accordingly, the fluorescent signals produced upon excitation of the biomarker probe label and the DNA stain are distinguishable from each other, meaning that both can be detected at the same time and that the signal from one does not modify or change the signal from the other. Each distinct label may produce signals that are distinguishable from any other label. For example, the cells may be stained with three fluorescent labels which produce three distinct fluorescent signals that are distinguishable from each other upon excitation.

The above types of data, e.g., the morphometric, biomarker, and non-specific cell data, may be obtained from the same aliquot of sample using any convenient protocol. In some instances, a flow cytometric protocol is employed which collects each type of data. Flow cytometry is a well-known methodology using multi-parameter data for identifying and distinguishing between different particle (e.g., cell) types i.e., particles that vary from one another terms of label (wavelength, intensity), size, etc., in a fluid medium. In flow cytometrically analyzing the sample prepared as described above, an aliquot of the sample is first introduced into the flow path of the flow cytometer. When in the flow path, the cells in the sample are passed substantially one at a time through one or more sensing regions, where each of the cells is exposed separately individually to a source of light at a single wavelength (or in some instances two or more distinct sources of light) and measurements of morphometric parameters, e.g., light scatter parameters, and/or biomarker parameters, e.g., fluorescent emissions, as desired, are separately recorded for each cell. The data recorded for each cell is analyzed in real time or stored in a data storage and analysis means, such as a computer, for later analysis, as desired.

More specifically, in a flow cytometer, the cells are passed, in suspension, substantially one at a time in a flow path through one or more sensing regions where in each region each cell is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 535 nm, 635 nm, and the like.

In series with a sensing region, detectors, e.g., light collectors, such as photomultiplier tubes (or "PMT"), image collectors (e.g., in the form of charge-coupled devices (CCDs)), etc., are used to record light that passes through each cell (generally referred to as forward light scatter), light that is reflected orthogonal to the direction of the flow of the cells through the sensing region (generally referred to as orthogonal or side light scatter) and fluorescent light emitted from the cells, if it is labeled with fluorescent marker(s), as the cells passes through the sensing region and is illuminated by the energy source. Each type of data that is obtained, e.g., forward light scatter (or FSC), orthogonal light scatter (SSC), and fluorescent emissions (FL1, FL2, etc.) and image, etc., comprise a separate parameter for each cell (or each "event").

Flow cytometers further include data acquisition, analysis and recording means, such as a computer, wherein multiple data channels record data from each detector for the morphometric and biomarker data emitted by each cell as it passes through the sensing region. The purpose of the analysis system is to classify and count cells wherein each cell presents itself as a set of digitized parameter values. In flow cytometrically assaying cells in methods of the invention, the flow cytometer may be set to trigger on a selected parameter in order to distinguish the cells of interest from background and noise. "Trigger" refers to a preset threshold for detection of a parameter. It is typically used as a means for detecting passage of cell through the laser beam. Detection of an event which exceeds the threshold for the selected parameter triggers acquisition of light scatter and fluorescence data for the cell. Data is not acquired for cells or other components in the medium being assayed which cause a response below the threshold. The trigger parameter may be the detection of forward scattered light caused by passage of a cell through the light beam. The flow cytometer then detects and collects the light scatter and fluorescence data for cell.

A particular subpopulation of interest is then further analyzed by "gating" based on the data collected for the entire population. To select an appropriate gate, the data is plotted so as to obtain the best separation of subpopulations possible. This procedure is typically done by plotting forward light scatter (FSC) vs. side (i.e., orthogonal) light scatter (SSC) on a two dimensional dot plot. The flow cytometer operator then selects the desired subpopulation of cells (i.e., those cells within the gate) and excludes cells which are not within the gate. Where desired, the operator may select the gate by drawing a line around the desired subpopulation using a cursor on a computer screen. Only those cells within the gate are then further analyzed by plotting the other parameters for these cells, such as fluorescence.

Any flow cytometer that is capable of obtaining both the morphometric and biomarker/non-specific cell data, e.g., as described above, from the same aliquot of a liquid sample may be employed. Of interest are those flow cytometer systems described in U.S. Pat. Nos. 6,211,955, 6,249,341, 6,256,096, 6,473,176, 6,507,391, 6,532,061, 6,563,583, 6,580,504, 6,583,865, 6,608,680, 6,608,682, 6,618,140, 6,671,044, 6,707,551, 6,763,149, 6,778,263, 6,875,973, 6,906,792, 6,934,408, 6,947,128, 6,947,136, 6,975,400, 7,006,710, 7,009,651, 7,057,732, 7,079,708, 7,087,877, 7,190,832, 7,221,457, 7,286,719, 7,315,357, 7,450,229, 7,522,758, 7,567,695, 7,610,942, 7,634,125, 7,634,126, 7,719,598; the disclosures of which are herein incorporated by reference.

Morphometric and biomarker/non-specific cell data obtained from the same aliquot of cervical cellular sample, e.g., as described above, is employed to whether the subject has a CIN lesion, as described above. Various combinations of morphometric, biomarker, and non-specific cell data may be employed in making a prediction of whether a subject has a CIN lesion. Combinations of interest include, but are not limited to, the following: a) nuclear to cytoplasmic (N/C) ratio analysis (e.g., to identify abnormal cells) coupled with quantification of E6, E7 mRNA; b) N/C ratio analysis coupled with cell cycle analysis as determined by DAPI staining and green fluorescence of the E6, E7 mRNA hybridization signal; c) N/C ratio analysis coupled with cell cycle analysis as determined by p16 staining and green fluorescence of the E6, E7 mRNA hybridization signal; d) N/C ratio analysis coupled with cell cycle analysis as determined by DAPI (or other DNA stain) staining, etc.

Increased, or high, N/C ratios include N/C ratios that are 0.25 or higher, 0.30 or higher, 0.4 or higher, 0.5 or higher, 0.6 or higher, 0.7 or higher, 0.8 or higher, 0.9 or higher, 0.95 or higher, etc.

In addition to N/C ratio, nuclear area (NA) assessment may be used as morphometric data. Cells in a cervical cell sample having an increased nuclear area, e.g., as compared to nuclei in normal intermediate squamous cells, can be identified cells as abnormal cells. Abnormal cells may have a nuclear area-to-nuclear area ratio (nuclear area of cell of interest/nuclear area of normal intermediate squamous cell) of 1.25 or more, 1.75 or more, 2.0 or more, 2.25 or more, 2.75 or more, 3.0 or more, 3.25 or more, 3.5 or more, etc. It is noted here that using standard microscopy observations, the accuracy of estimating nuclear area is low (see, e.g., Schmidt et al., 2008, "Visual estimates of nucleus-to-nucleus ratios: can we trust our eyes to use the Bethesda ASCUS and LSIL size criteria?" Cancer 114(5):287-93.

Aspects of the present invention provide a more accurate and reproducible assessment of nuclear area.

Additional data parameters may also be employed in analyzing the cells in the cervical cell sample, including side (orthogonal) light scatter, forward scatter, and electronic volume (EV; a measure of cell size; based on the Coulter principle). Such parameters find use in identifying populations or sub-populations of cells in the sample that are to be analyzed for the presence of abnormal cells (see, e.g., FIG. 6 and its description herein). For example, analysis of EV and DNA content (e.g., using DAPI) allows the differentiation of enucleated from nucleated squamous cells.

In some instances, the methods include determining that the assayed cellular sample includes cancerous cells. In these embodiments, the methods include identifying the presence of one or more cancerous cells in the sample, where the identification is made based on morphometric and biomarker data, e.g., as described above. Such embodiments may or may not include predicting the presence of CIN in a subject, since the methods of these embodiments identify the presence of actual cancerous cells in the sample.

In some instances, the prediction of the presence of a CIN lesion is made within a short period of time following introduction of the sample into the cytometer. Accordingly, results may be provided to a user in a period of 6 hours or less, such as 3 hours or less, e.g., 2 hours or less, including 1 hour or less. Where desired, the overall assay time which ranges from obtainment of the sample from the subject to delivery of the result to the subject is 6 hours or less, such as 5 hours or less, e.g., 4 hours less, including 3 hours or less, e.g., 2 hours or less.

In some instances, the methods further include performing further analysis of a subject if the methods result in a prediction of a CIN lesion in the subject. For example, where methods of the invention result in prediction of a CIN2+ lesion in a subject, the methods may then further include providing a recommendation to a subject that further action be taken, e.g., in the form of further diagnostic procedures, such as biopsy. In some instances, the methods include taking further diagnostic action. Further diagnostic action may include a colposcopy, in which a magnified visual inspection of the cervix is performed to identify abnormal cells on the surface of the cervix. If the biopsy indicates that cancer or pre-cancerous lesions may be present, further diagnostic and treatment procedures may be taken, such as loop electrical excision procedure (LEEP) and conization, in which the inner lining of the cervix is removed to be examined pathologically.

While the methods are suitable for use with a variety of different female mammalian subjects, of interest are use of the methods with human female subjects, such as human female subjects of 10 years age or older, e.g., 15 years age or older, including 20 years age or older.

Devices and Systems

Aspects of the invention further include systems for use in practicing the subject methods. Systems of interest include a flow cytometer configured to assay a liquid sample for both morphometric and biomarker data, e.g., as described above. Flow cytometers of interest include, but are not limited, to those devices described in U.S. Pat. Nos. 4,704,891; 4,727,029; 4,745,285; 4,867,908; 5,342,790; 5,620,842; 5,627,037; 5,701,012; 5,895,922; and 6,287,791 which, if necessary, are modified to include the ability to obtain image data as described above, as well as those cytometers described in U.S. Pat. Nos. 6,211,955, 6,249,341, 6,256,096, 6,473,176, 6,507,391, 6,532,061, 6,563,583, 6,580,504, 6,583,865, 6,608,680, 6,608,682, 6,618,140, 6,671,044, 6,707,551, 6,763,149, 6,778,263, 6,875,973, 6,906,792, 6,934,408, 6,947,128, 6,947,136, 6,975,400, 7,006,710, 7,009,651, 7,057,732, 7,079,708, 7,087,877, 7,190,832, 7,221,457, 7,286,719, 7,315,357, 7,450,229, 7,522,758, 7,567,695, 7,610,942, 7,634,125, 7,634,126, 7,719,598; the disclosures of which are herein incorporated by reference.

In some instances, the flow cytometer includes: a flow channel; at least a first light source configured to direct light to an assay region of the flow channel (where in some instances the cytometer includes two or more light sources); a first detector configured to receive light of a first wavelength from the assay region of the flow channel; and a second detector configured to receive light of a second wavelength from the assay region of the flow channel; and an image detector configured to obtain image data of cells. Such a cytometer would have at least two detection channels in addition to the image detector. In some instances, the device may include more than two detection channels, e.g., 3 or more, 4 or more, 5 or more, 10 or more, etc.

Aspects of the invention further include signal processing module configured to receive the morphometric and biomarker data from the first and second detectors and output a result of a prediction of whether a subject has a cervical intraepithelial neoplasia (CIN) lesion based on both the morphometric data and biomarker data. The signal processing module may be integrated into the cytometer as a single device, or distributed from the cytometer where the signal processing module and cytometer are in communication with each other, e.g., via a wired or wireless communication protocol.

Accordingly, aspects of the invention further include systems, e.g., computer based systems, which are configured to predict the presence of a CIN lesion in a subject, e.g., as described above. A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Embodiments of the subject systems include the following components: (a) a communications module for facilitating information transfer between the system and one or more users, e.g., via a user computer, as described below; and (b) a processing module for performing one or more tasks involved in the quantitative analysis methods of the invention.

In certain embodiments, a computer program product is described comprising a computer usable medium having control logic (computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In some instances, the systems may further include a reaction mixture derivative thereof (e.g., washed cells produced therefrom), where the reaction mixture is prepared as described above, e.g., by combining a sample, one or more labeled biomarker probes and, optional, a non-specific stain.

Utility

The subject methods and systems find use in a variety of different applications where detection prediction of a CIN lesion in a subject is desired. Such applications include both research and diagnostic applications, e.g., applications where a subject is diagnosed with respect to the presence of or propensity to develop cervical cancer, e.g., as described above. The clinical utility of the methods and systems described herein provide powerful tools to detect and screen HPV related pathogenesis and cervical cancer development in both early and late stages, thus allowing therapeutic intervention to prevent disease progression as well as a chance to provide early treatment. In addition, the subject methods and systems finds use in the prognosis or risk assessment of an HPV-related disease or condition, for monitoring of the evolution of an HPV-related disease or condition, and for monitoring the efficiency of an anti-HPV drug or treatment, such as e.g., an anti-HPV vaccine or an anti-HPV vaccine candidate.

Computer Related Embodiments

Aspects of the invention further include a variety of computer-related embodiments. Specifically, the data analysis methods described in the previous sections may be performed using a computer. Accordingly, the invention provides a computer-based system for analyzing data produced using the above methods in order to detect or predict a CIN lesion.

In certain embodiments, the methods are coded onto a physical computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. Of interest as media are non-transitory media, i.e., physical media in which the programming is associated with, such as recorded onto, a physical structure. Non-transitory media does not include electronic signals in transit via a wireless protocol.

With respect to computer readable media, "permanent memory" refers to memory that is permanent. Permanent memory is not erased by termination of the electrical supply to a computer or processor. Computer hard-drive, CD-ROM, floppy disk and DVD are all examples of permanent memory. Random Access Memory (RAM) is an example of non-permanent memory. A file in permanent memory may be editable and re-writable.

Kits

In yet another aspect, the present invention provides kits for practicing the subject methods, e.g., as described above. The subject kits may include labeled biomarker probes, e.g., as described above. In addition, the kits may include non-specific stains, as described above. In addition, the kit may include one or more additional compositions that are employed, including but not limited to: buffers, diluents, fixing reagents, permeabilizing reagents, etc., which may be employed in a given assay. Kits may further include sample obtainment devices, e.g., cervical brooms, as described above. The above components may be present in separate containers or one or more components may be combined into a single container, e.g., a glass or plastic vial.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Figure 2:
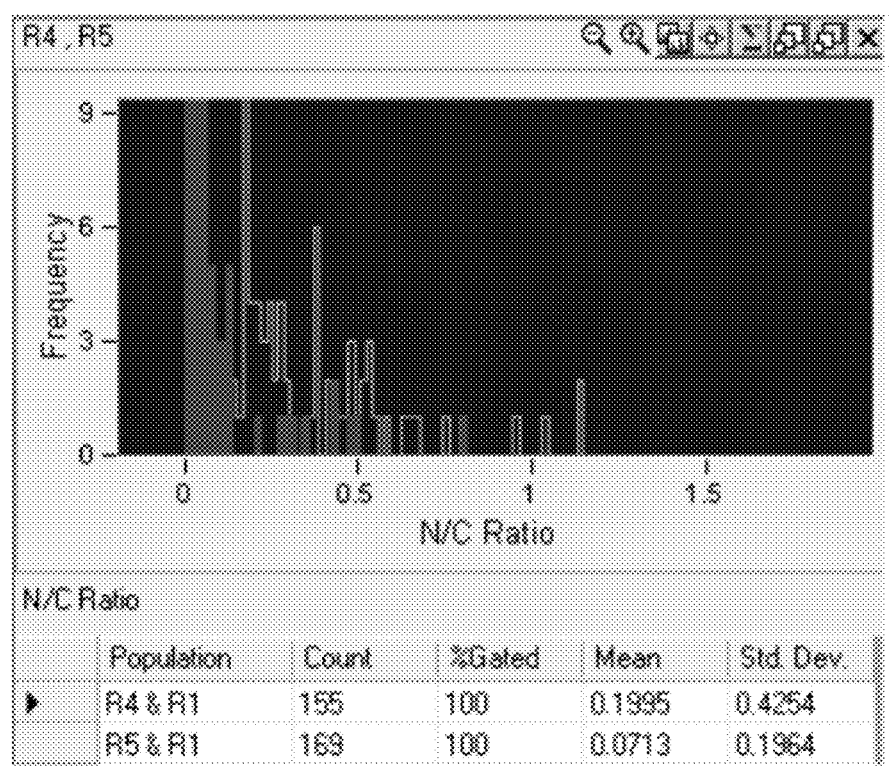
FIG. 2 shows identification of abnormal cells in a LBC specimen by N/C (nuclear to cytoplasmic) ratio analysis using the instrument set up as in FIG. 1. Increased N/C ratios are indicative of abnormal cells.
Figure 3A:
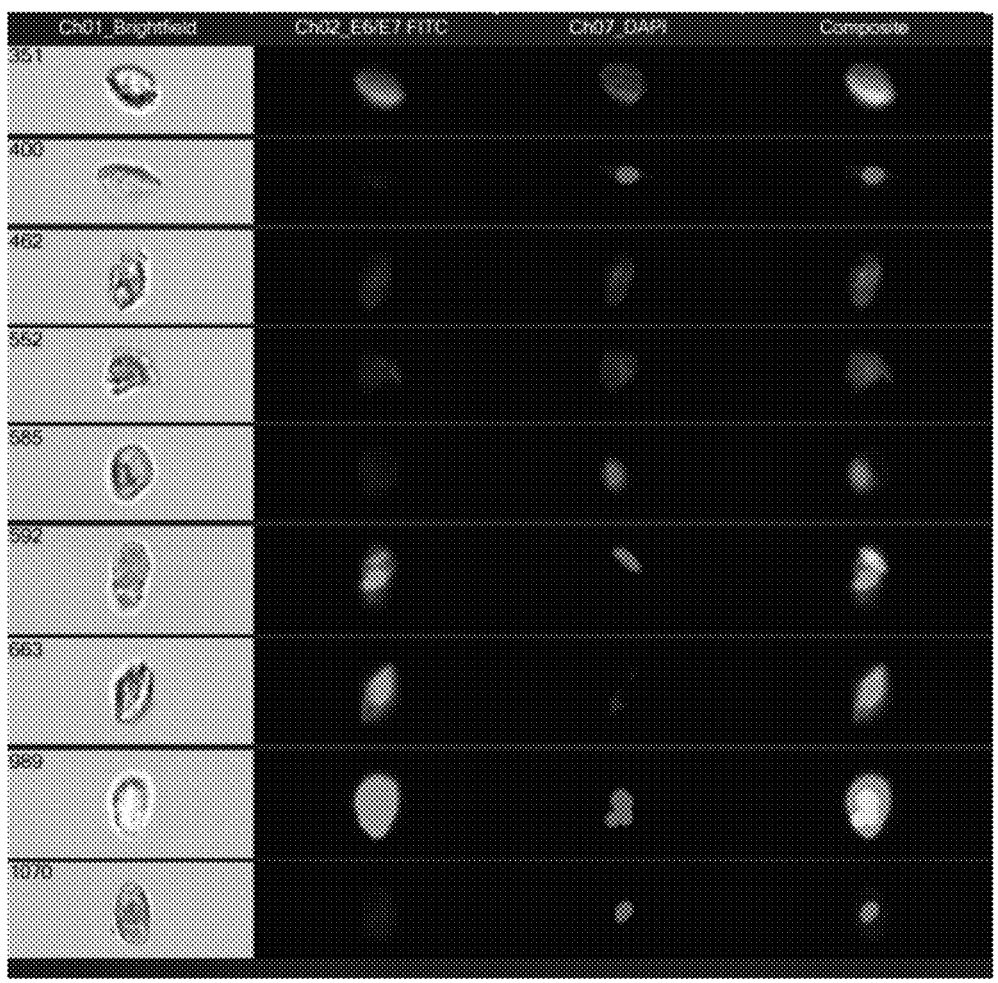
FIGS. 3A and 3B show exemplary data obtained for single cells in a LBC specimen. For each cell, a brigthfield image, an image showing E6/E7 mRNA hybridization (FITC), an image showing the DNA quantification (DAPI), and an image showing a composite of the E6/E7 and DAPI images are shown.
Figure 3B:
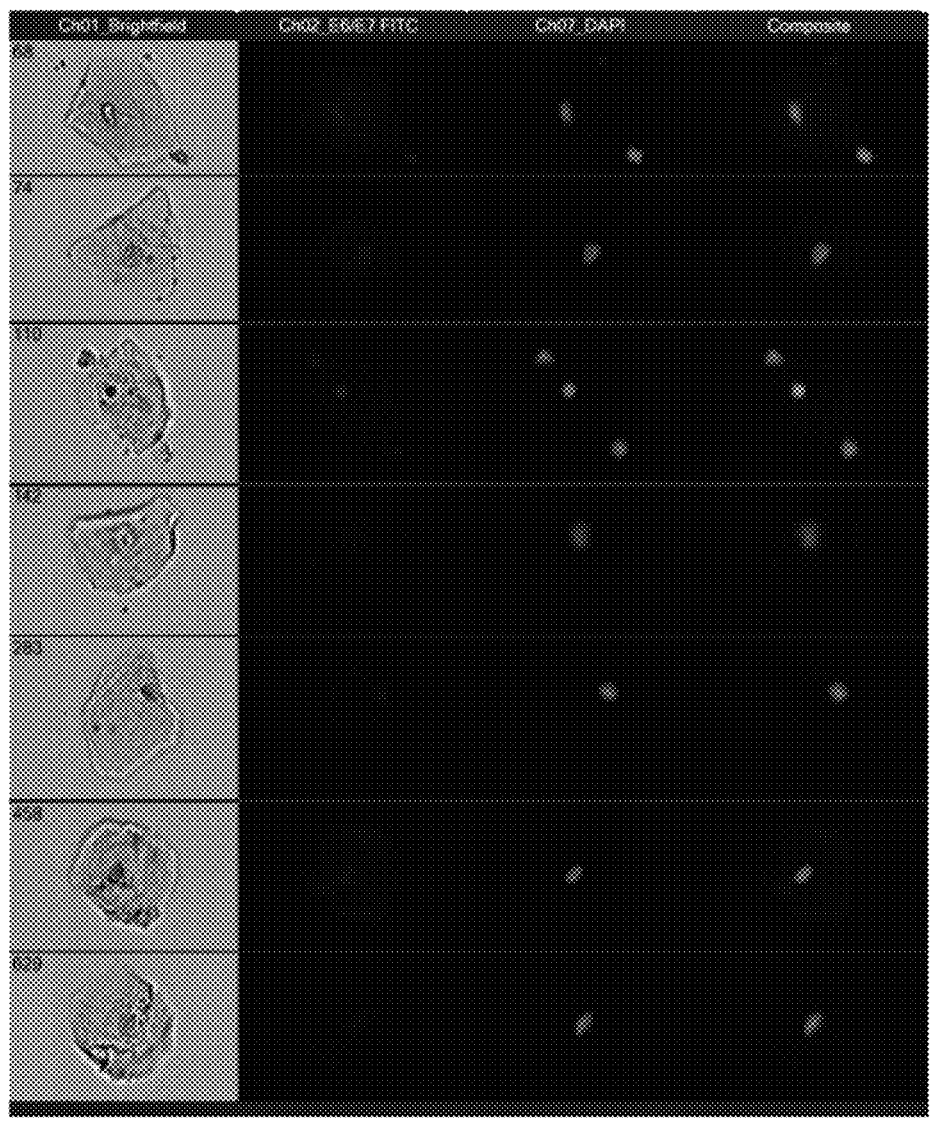

A 1 ml sample aliquot of the liquid-based cervical cytology (LBC) specimen obtained was and centrifuged at 1000×g for 5 minutes at room temperature. The resultant cell pellet was washed twice in phosphate buffer saline (PBS), pH 7.4 and the cells were fixed and permeabilized for 1 h at room temperature using IncellFP (Incelldx, Menlo Park, Calif.). The resultant fixed and permeabilized cells were washed twice using two different pre-hybridization buffers (PBS and 2×SSC) and a hybridization cocktail was prepared by mixing hybridization buffer (5×SSC, 30% formamide) with a fluorescence-labeled HPV E6, E7 mRNA probe cocktail for all known high risk HPV types (the probe cocktail was from the those found in the probe cocktail of the HPV OncoTect™ E6, E7 mRNA Detection Kit (incellDx, Menlo Park, Calif.). The hybridization reaction was performed in a preheated 43±1° C. water bath for 30 minutes and was followed by stringency washing of cells with two post-hybridization buffers (2×SSC, Triton X-100 and 0.1× SSC, Triton X-100) in order to remove the unbound probe. The cells were washed in 1 ml PBS containing 2% fetal calf serum and re-suspended in 60 μl PBS, 0.05% Triton X-100, and 1 μg/ml DAPI. Prior to running on the instrument, 200 μl 10 μM EDTA in PBS was added. The samples were homogenized with a syringe and run on an ImageStream instrument (Amnis Inc, Seattle, Wash.). The instrument was set-up to distinguish intact single cells using Aspect Ratio versus Area dot plot, e.g., as shown in FIG. 1. This setting allowed: (1) identification of abnormal cells by N/C (nuclear to cytoplasmic) ratio analysis (see e.g., FIG. 2); and (2) quantification of E6, E7 mRNA as determined by DAPI staining and green fluorescence of the E6, E7 mRNA hybridization signal (see FIGS. 3A and 3B).

Figure 4:
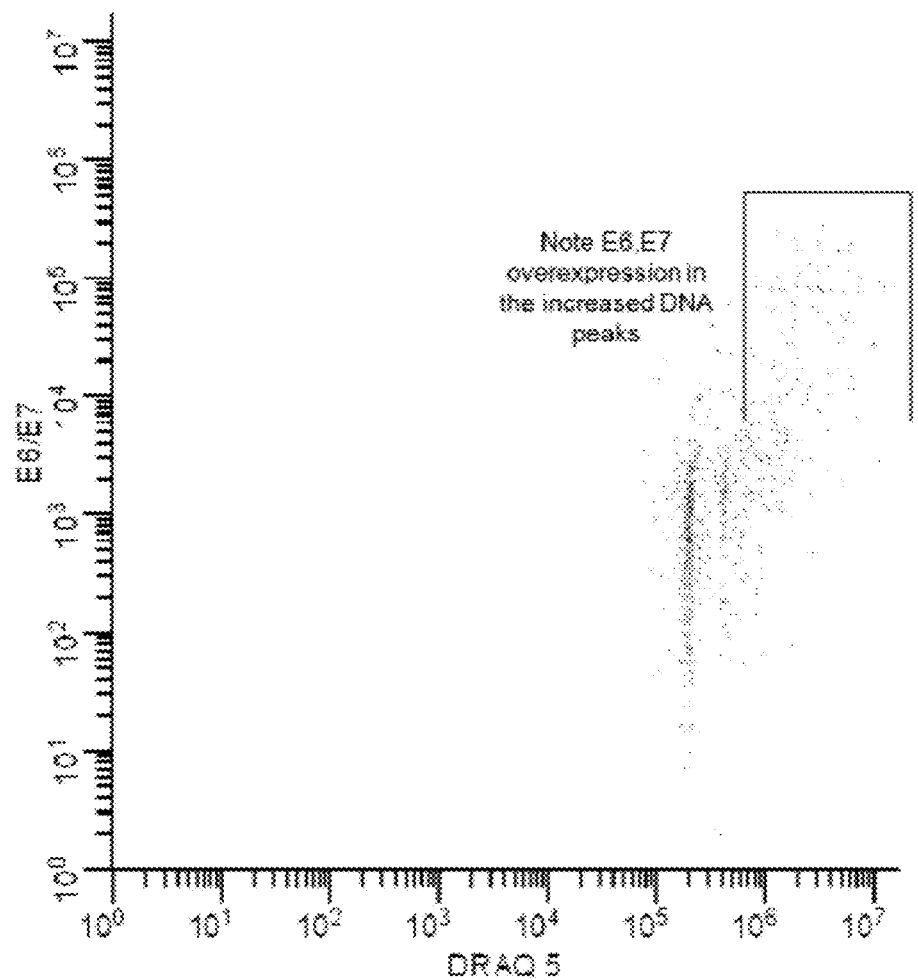
FIG. 4 is a dot plot showing that overexpression of E6/E7 mRNA is found in cells having increased DNA content. Cell cycle analysis was determined using a DNA-staining reagent (DAPI; X-axis) and E6/E7 mRNA was detected by hybridization of E6/E7 mRNA probes (FITC; Y-axis). Abnormal cells (having E6, E7 overexpression and increased DNA content) are indicated in the gate.

Alternatively, cell cycle analysis as determined by a DNA-staining reagent (e.g., DAPI or DRAQ5 staining of the cells) and green fluorescence of the E6, E7 mRNA hybridization signal can be used to detect abnormal cells. For example, as can be seen in the histogram in FIG. 4, overexpression of E6/E7 mRNA (Y-axis) is found in cells having increased DNA content (X-axis; DNA stain is DRAQ5).

Combined use of morphometric measurements consistent with accepted slide based criteria in Table 1 and E6, E7 mRNA overexpression on a cell-by-cell basis all performed on cells while in suspension increased the sensitivity and specificity for detection of CIN 2+ to >95% and >90% respectively. This performance in a single assay greatly exceeds the test performance of the PAP smear and HPV DNA combined for the detection of CIN 2+ lesions.

This approach can be used substituting a p16 antibody for E6, E7 mRNA detection, or substituting E6, E7 mRNA probes with probes directed at specific microRNAs or chromosome alterations 3q-associated with cervical cancer, or substituting E6, E7 directed antibodies for E6, E7 mRNA probes.

Figure 5A:
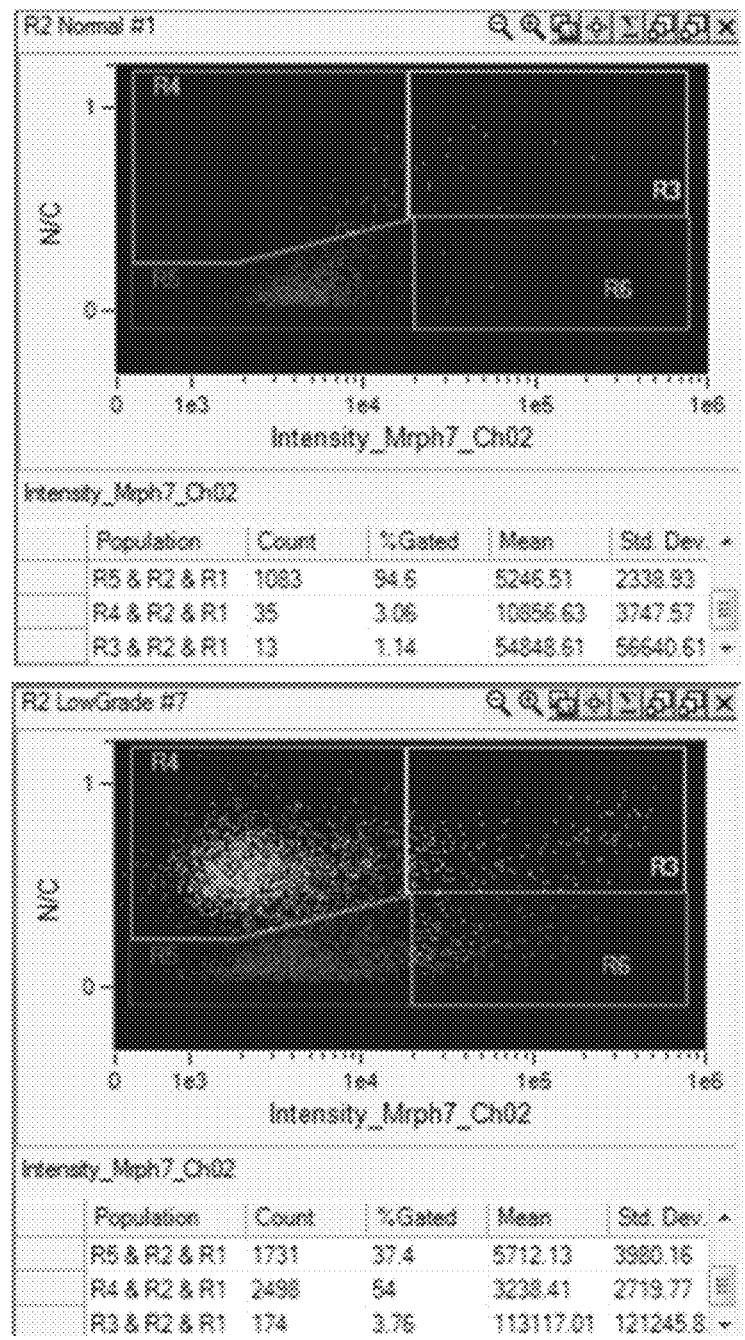
FIGS. 5A and B show dot plots showing N/C ratios (Y axis) and DNA content (x axis) of LBC specimens to identify abnormal cells.
Figure 5B:
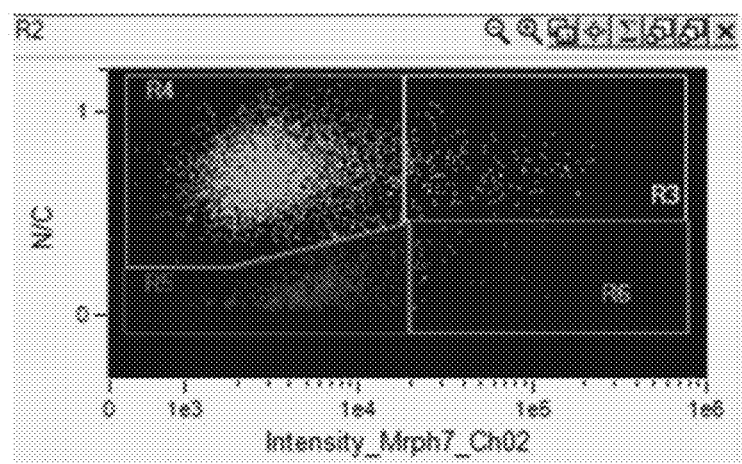
FIG. 5B shows dot plots of N/C ratios versus DNA content of HSIL cervical cells (top and bottom panels). This alternative uses only 1 staining reagent, i.e., the non-specific DNA-staining reagent.
Figure 5B:
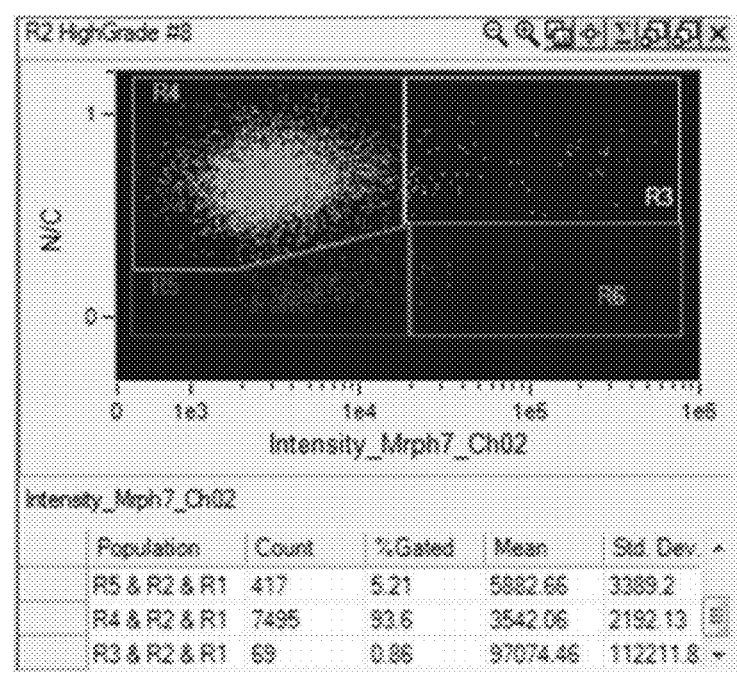

As an additional alternative, cell cycle analysis as determined by a DNA-staining reagent coupled with morphometric measurements, e.g., nuclear/cytoplasmic ratio of the cells, can be used to detect abnormal cells. For example, FIGS. 5A and 5B show histograms of N/C ratios (Y-axis) versus DNA content of normal cervical cells (FIG. 5A, top panel), LSIL cervical cells (FIG. 5A, bottom panel), and HSIL cervical cells (FIG. 5B, both panels). This alternative uses only 1 staining reagent, i.e., the non-specific DNA-staining reagent.

Furthermore, as shown in Table 2 below, we have found that degree of nucleation of squamous cells in the sample, as determined by using a DNA staining reagent, corresponds with the severity of the cytologic abnormality. Specifically, an increase in the percent nucleation of the squamous cells in the sample corresponds to an increased severity of the cytologic abnormality. In Table 2, normal squamous cells had a % nucleation of about 50%, LSIL squamous cells had a % nucleation of about 80%, and HSIL squamous cells had a % nucleation above 90%. As such, a percent nucleation for squamous cells in a sample from a subject of about 80% or higher indicates that the subject has a cervical intraepithelial neoplasia (CIN) lesion (e.g., LSIL or HSIL), where a percent nucleation of about 90% or higher in the sample indicates that the subject has a high grade squamous epithelial lesion (HSIL).

TABLE 2

Nucleation of the Squamous Cell Population as a Determinate of Abnormal Pap Smear Diagnosis

| Sample group | Cytology | % nucleated |
|---|---|---|
| 1 | Normal | 47.33 |
| 2 | LSIL | 82.66 |
| 3 | HSIL | 94.38 |
| 4 | HSIL | 93.41 |

Figure 6:
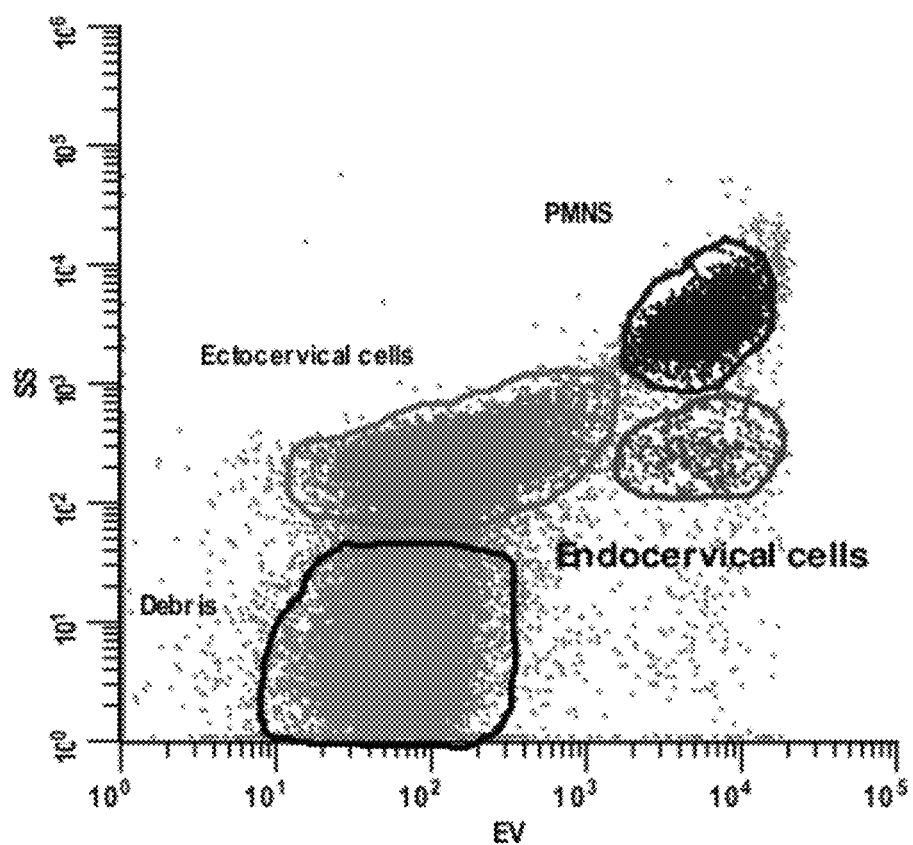
FIG. 6 shows a dot plot of combined side (orthogonal) light scatter (Y axis) and electronic volume (X axis) of cells in a cervical cytology sample. This plot shows that different cells in the sample can be delineated using these morphometric parameters. The four different gates identify debris, ectocervical cells, endocervical cells, and polymorphonuclear leukocytes (PMNS). Such gating can be employed to gate for cells of interest to analyze according to aspects of the present invention.

LSIL—low grade squamous epithelial lesion
HSIL—high grade squamous epithelial lesion Cervical cell samples may include cell types (and other debris) that are not relevant to the screening assays described herein, and as such it would be advantageous to exclude them from the analysis. FIG. 6 shows a dot plot of combined side (orthogonal) light scatter (Y axis) and electronic volume (X axis) of cells in a cervical cytology sample. This plot shows that different cells (and other components) in the sample can be delineated using these morphometric parameters. The four different gates identify debris, ectocervical cells, endocervical cells, and polymorphonuclear leukocytes (PMNS). Gating can be employed to identify cells of interest to screen according to aspects of the present invention (e.g., endocervical and/or ectocervical cells).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of detecting whether a subject has a cervical intraepithelial neoplasia (CIN) lesion that is a CIN2+ lesion, the method comprising:
   contacting a cervical cell sample from the subject with a fluorescently labeled biomarker probe that specifically binds to a cervical cancer biomarker and a fluorescent DNA-staining reagent to produce a labeled liquid sample of cervical cells;
   flow cytometrically analyzing the labeled liquid sample of cervical cells to obtain data comprising per cell morphometric data, per cell biomarker data based on the fluorescently labeled biomarker probe and per cell DNA content data based on the fluorescent DNA-staining reagent; and
   detecting from the per cell morphometric data, the per cell biomarker data and the per cell DNA content data whether the subject has a CIN2+ lesion.

2. The method according to claim 1, wherein the detecting is characterized by a sensitivity of 85% or higher.

3. The method according to claim 1, wherein the detecting is characterized by a specificity of 85% or higher.

4. The method according to claim 1, wherein the analyzing comprises flowing the sample past an illumination source and one or more optical detectors.

5. The method according to claim 4, wherein the morphometric data comprises data selected from the group consisting of: forward light scatter data, side light scatter data, image data and combinations thereof.

6. The method according to claim 1, wherein the biomarker data comprises per cell biomarker quantitation data.

7. The method according to claim 1, wherein the cervical cancer biomarker is a nucleic acid or protein.

8. The method according to claim 7, wherein the cervical cancer biomarker is a nucleic acid.

9. The method according to claim 8, wherein the nucleic acid is an HPV nucleic acid.

10. The method according to claim 9, wherein the HPV nucleic acid is an HPV E6 or E7 nucleic acid.

11. The method according to claim 7, wherein the cervical cancer biomarker is a protein.

12. The method according to claim 11, wherein the protein is p16.

13. The method according to claim 11, wherein the protein is E6 or E7.

14. The method according to claim 11, wherein the method comprises contacting the initial cervical cell sample with two or more different fluorescently labeled biomarker probes that each specifically bind to a different cervical cancer biomarker.

15. The method according to claim 1, wherein cells in the initial cervical cell sample are fixed and permeabilized prior to being contacted with a fluorescently labeled biomarker probe that specifically binds to a cervical cancer biomarker.

16. The method according to claim 1, wherein the method further comprises recommending a cervical biopsy if abnormal cells are determined to be present in the sample.

17. A method of detecting whether a subject has a cervical intraepithelial neoplasia (CIN) lesion that is a CIN2+ lesion, the method comprising:
   (a) providing a biomarker labeled liquid sample of cervical cells in suspension by a method comprising:
      (i) combining an initial cervical cell sample with fixation and permeabilization reagents to fix and permeabilize the cells; and
      (ii) contacting the fixed and permeabilized cells with a fluorescently labeled biomarker probe that specifically binds to a cervical cancer biomarker and a fluorescent DNA-staining reagent;
   (b) obtaining per cell morphometric data, per cell DNA content data based on the fluorescent DNA-staining reagent and per cell biomarker quantitation data based on the fluorescently labeled biomarker probe from the liquid sample by flowing the liquid sample past an illumination source and one or more optical detectors in a flow cytometer; and
   (c) detecting from the morphometric data, the DNA content data and per cell biomarker quantitation data whether the subject has a CIN2+ lesion.

18. A method of determining the presence of a cancerous cervical cell in sample from a subject, the method comprising:
   contacting a cervical cell sample from the subject with a fluorescently labeled biomarker probe that specifically binds to a cervical cancer biomarker and a fluorescent DNA-staining reagent to produce a labeled liquid sample of cervical cells;
   flow cytometrically analyzing the labeled liquid sample of cervical cells to obtain data comprising per cell morphometric data, per cell biomarker data based on the fluorescently labeled biomarker probe and per cell DNA content data based on the fluorescent DNA-staining reagent; and
   determining that a cancerous cell is present in the sample when:
      (i) a cell of the liquid sample is determined to be abnormal based on the per cell morphometric data; and
      (ii) the cell of the liquid sample is determined to be abnormal based on the per cell biomarker data and the per cell DNA content data.

19. The method according to claim 1, wherein the per cell morphometric data is at least one of: per cell nuclear to cytoplasmic ratio (N/C), and per cell nuclear area.

20. The method according to claim 1, wherein the method further comprises, prior to the step of detecting, determining whether abnormal cells are present in the liquid sample based on:
   (i) the morphometric data, and
   (ii) the per cell biomarker data, the per cell DNA content data, or both;
   and wherein a CIN2+ lesion is detected when abnormal cells are determined to be present in the liquid sample.

21. The method according to claim 20, wherein a cell of the liquid sample is determined to be abnormal when the cell of the liquid sample is determined to be abnormal based:
   (i) the per cell morphometric data;
   (ii) the per cell biomarker data; and
   (iii) the per cell DNA content data.

22. The method according to claim 21, wherein the per cell morphometric data is per cell nuclear to cytoplasmic ratio (N/C).

23. The method according to claim 22, wherein the cell of the liquid sample is determined to be abnormal based on the per cell morphometric data when the nuclear to cytoplasmic ratio of the cell is 0.25 or higher.

24. The method according to claim 18, wherein the per cell morphometric data is per cell nuclear to cytoplasmic ratio data.

25. The method according to claim 24, wherein the cell of the liquid sample is determined to be abnormal based on the morphometric data when the nuclear to cytoplasmic ratio is 0.25 or higher.

26. The method according to claim 1, wherein: (i) per cell morphometric data, (ii) per cell biomarker data, and (iii) per cell DNA content data are collected for each cell from which data is obtained.

27. The method according to claim 1, wherein the per cell biomarker data comprises data on a HPV gene biomarker or an HPV gene expression product biomarker.

28. The method according to claim 7, wherein biomarker is selected from the group consisting of: HPV gene L1, HPV gene L2, HPV gene E2, HPV gene E4, HPV gene E5, HPV gene E6, a HPV gene expression product of HPV gene L1, a HPV gene expression product of HPV gene L2, a HPV gene expression product of HPV gene E2, a HPV gene expression product of HPV gene E4, a HPV gene expression product of HPV gene E5, a HPV gene expression product of HPV gene E6, p14, $p15^{INK4b}$, $p18^{INK4c}$, $p19^{INK4d}$, $p21^{WAF1/CIP1}$, $p27^{KIP1}$, $p14^{ARF}$, a microRNA associated with cervical cancer, and a chromosome alteration associated with cervical cancer.

29. The method according to claim 1, wherein the detecting step detects whether the subject has a CIN2+ lesion and whether the subject has a CIN1 lesion.

\* \* \* \* \*